United States Patent
Van Leer

(10) Patent No.: US 8,313,447 B2
(45) Date of Patent: Nov. 20, 2012

(54) EXTENDED USE HOME UTERINE ACTIVITY MONITOR

(76) Inventor: Thomas James Van Leer, Santa Clara, CA (US)

(*) Notice: Subject to any disclaimer, the term of this patent is extended or adjusted under 35 U.S.C. 154(b) by 178 days.

(21) Appl. No.: 12/849,105

(22) Filed: Aug. 3, 2010

(65) Prior Publication Data

US 2012/0035508 A1 Feb. 9, 2012

(51) Int. Cl.
*A61B 5/103* (2006.01)
*A61B 5/117* (2006.01)

(52) U.S. Cl. .................. 600/588; 600/591; 600/595

(58) Field of Classification Search .............. 600/304, 600/587, 588, 591, 595
See application file for complete search history.

(56) References Cited

U.S. PATENT DOCUMENTS

| | | | |
|---|---|---|---|
| 8,075,500 B2* | 12/2011 | Berger et al. ............... | 600/591 |
| 2008/0119896 A1* | 5/2008 | Wong et al. ................. | 607/2 |
| 2009/0240131 A1* | 9/2009 | Lu et al. ..................... | 600/372 |
| 2010/0312088 A1* | 12/2010 | Browne ....................... | 600/407 |

* cited by examiner

*Primary Examiner* — Max HIndenburg
*Assistant Examiner* — Jonathan M Foreman
(74) *Attorney, Agent, or Firm* — Stephen E. Zweig

(57) ABSTRACT

A uterine activity monitoring device and method for monitoring uterine activity on a nearly continuous basis. The device may comprise a belt configured to fit around a pregnant patient's abdomen, with a plurality of, uterine contraction sensors. These sensors may be protruding contraction sensing buttons, disposed generally perpendicular to the patient's skin. In order to avoid signal distortions caused by patient movement, the belt will often have at least one ambient motion sensor configured to monitor non-uterine contraction movements and produce background movement signals. These ambient motion sensors may be accelerometers and stretch or pressure disposed generally parallel to the patient's skin. The device will have an onboard processor communicate wirelessly with a variety of external monitoring and management systems, such as wrist worn monitors, cell phones, and remote patient management websites.

9 Claims, 5 Drawing Sheets

EXTENDED USE HOME UTERINE ACTIVITY MONITOR

BACKGROUND OF THE INVENTION

1. Field of the Invention

The invention is in the general area of home uterine activity monitoring devices and methods.

2. Description of the Related Art

Human pregnancy should ideally last about 38 weeks from conception. However often it does not and infants born before about 37 weeks of gestation are at high risk for medical complications and mortality. The care and treatment of these premature infants imposes enormous costs upon the medical system. Indeed the treatment of extremely low birth weight infants can occasionally result in over a million dollars of medical costs for each infant.

In addition to the trauma, suffering, and financial distress that such premature births place on the infant's family, surviving premature infants are at increased risk for lifelong problems, including cerebral palsy, vision loss, hearing loss, and mental retardation.

In order to help prevent premature births, it can be important to monitor the uterus for abnormal contractions and other signs of preterm labor. If such abnormal contractions and other signs of preterm labor can be detected in time, various anti-contraction medications, called tocolytic agents may be administered to slow down or stop preterm labor. These tocolytic drugs include Terbutaline, Ritodrine, Nifedipine, and others. Although many of these drugs may only delay subsequent labor by a number of days, this extra time can make all the difference for preterm infant survival. Premature infant lungs are often not capable of functioning properly in an air environment, but if the physician knows in advance that early labor will be coming in a few days, fetal lung maturity can be accelerated over a several day period by administering drugs such as betamethasone.

Unfortunately tocolytic drugs have side effects, such as maternal cardiac arrhythmias, and a number of these drugs also have side effects on the fetus as well. Thus these drugs are generally not given unless it is clear that there really are premature contractions.

Unfortunately, without instrumentation, patients often have difficulty in distinguishing between normal Braxton-Hicks contractions, the onset of abnormal uterine contractions such as preterm labor. As a result, in order to better detect preterm labor and other abnormal uterine contractions, in the early 1990's, various types of uterine contraction monitors, often called tocodynamometer devices, or Home Uterine Activity Monitors (HUAM), were introduced to the market.

These early HUAM devices were rather cumbersome however. The standard method of use was to instruct the patient to put the HUAM device on for an hour, collect data, then remove the HUAM device, connect the device to a telephone and transmit the data to a center on a twice daily basis.

After an initial burst of enthusiasm regarding the utility of HUAM, work since then has tended to discourage this approach. In 2001, the American College of Obstetrics and Gynecology published a position statement that cast doubt on the efficacy of these devices, and other studies since then have also been negative. At present, most major medical insurance carriers do not provide coverage for HUAM devices.

BRIEF SUMMARY OF THE INVENTION

At present, skilled workers in the field tend to believe that HUAM is of minimal or no practical value in the management of preterm labor. In this specification, devices and methods intended to overcome the problems of prior art HUAM monitoring methods are disclosed.

In one embodiment, the invention may be a uterine activity monitor device capable of being comfortably worn throughout the day, often on a nearly continual basis. Here continual basis is defined to mean an appreciable part of the day, such as more than a third of the day (i.e. more than 8 hours), such as more than 12 hours, more than 15 hours, more than 18 hours, or more than 21 hours a day. This monitoring device may comprise a belt, such as an elastic belt, configured to fit around a pregnant patient's abdomen. This belt will have at least one, and often a plurality of, uterine contraction sensors configured to monitor uterine contractions and produce uterine contraction signals. In order to avoid signal distortions caused by patient movement, which will be inevitable for devices intended to be worn throughout the day, this belt will often have at least one ambient motion sensor configured to monitor non-uterine contraction movements and produce other movement (background movement) signals. The device will often have a processor, such as a microprocessor and associated software, configured to correct the uterine contraction signals for distortions caused by the patient's movement. Ambient of background patient movement may be detected by other (non-uterine contraction) movement (background movement) sensors. The device may also often have either an onboard memory to store these various signals, a wireless transmitter or transceiver configured to transmit these signals to outside devices, or both.

In some embodiments, the uterine contraction sensors will often consist of at least one, and often a plurality of motion sensors such as stretch sensors (e.g. elastic stretch sensors that change resistance or capacitance when stretched), pressure sensors (e.g. micro-electromechanical systems (MEMS) pressure sensors), often configured in an orientation to more specifically respond to uterine contraction motion and pressure. The ambient or background motion sensors will often consist of at least one, and often a plurality of motion sensors such as stretch sensors which may be configured in an orientation to more specifically respond to motion other than uterine contraction motion and pressure. The ambient motion sensors may also include patient movement sensors such as accelerometers (e.g. MEMS accelerometers) and the like.

The uterine contraction movements will often be wirelessly transmitted to outside devices such as monitoring wristwatch devices, "smart" cellular phone devices which may be configured with contraction monitoring software, or to wireless gateways that in turn may transfer the data over networks such as the Internet to remote telemedicine devices, healthcare workers, and other monitoring devices.

DETAILED DESCRIPTION OF THE INVENTION

Figure 1:
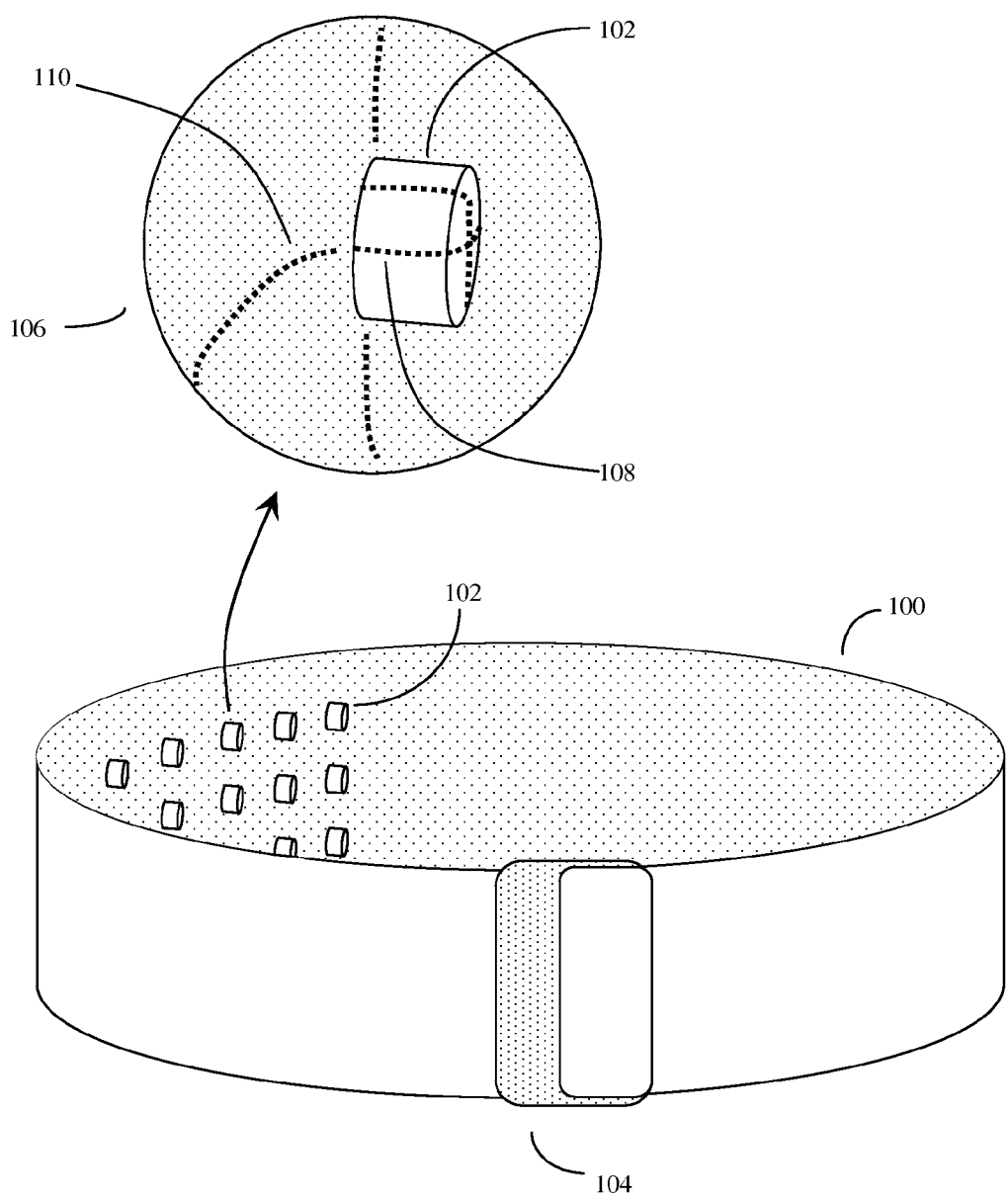
FIG. 1 shows a drawing of the flexible long-duration wear home uterine activity monitor.

The invention is based on the insight that a major contributing factor to the failure of earlier generation HUAM devices to become medically accepted is that these prior art HUAM devices only monitored uterine activity about 2 hours a day—about 8% of the time. An additional problem was that because patients would often wear these prior art HUAM devices on a regular daily schedule, these limited wear HUAM devices would tend to miss unusual patterns of uterine activity that might only be manifested during certain situations or times of the day. For example, if the pattern of abnormal uterine contractions only started in response to certain limited situations, such as after meals of after mild exercise the earlier generation HUAM devices could easily miss these events. Monitoring uterine activity only 8% of the time by necessity means that 92% of the time, uterine activity was not being monitored. Thus the efficacy of the earlier HUAM monitoring systems suffered as a result.

In order to catch a much greater proportion of the uterine activity events, it is necessary to rethink the design of uterine activity monitoring devices. If the device is to be worn nearly all day, possibly for weeks at a time, the device must be both comfortable and configured to cope with the large amount of ambient background movement that occurs in the everyday home environment. For example, the patient will frequently be bending, stretching, standing up, sitting down, exercising, and the like, and during this time, the large ambient motion caused by these activities will likely swamp the comparatively smaller signal produced by uterine contraction.

In order to better distinguish uterine contraction from normal patient motion or ambient activity (ambient motion), often it will be useful to use a device with a plurality of soft, semi-soft, or semi-rigid projecting or protruding "fingers", "buttons" or "probes" (here called contraction sensing buttons) designed, when worn on the underside of a belt, which often will be an elastic belt, to put mild pressure on the skin of the patient's abdomen. This mild pressure may be achieved by, for example, making the belt an elastic belt. In some embodiments, the elastic belt may have a pressure monitor attached to its buckle so that the patient can adjust the belt to put the optimal amount of pressure on the various contraction sensing buttons. These contraction sensing buttons or projections will often be positioned strategically to match the position of the underlying uterus.

The belt will generally be taken on and off by the patient on a daily basis, and additionally the uterus and regions of the uterus where uterine contractions of interest will occur will vary during pregnancy. Thus often it will be useful to put a plurality of these contraction sensing buttons on the underside of the belt, and deliver the signal from these various contracting sensing buttons to a signal processing device, such as a microprocessor. The microprocessor and supporting software may then selectively process the uterine contraction signals from the various contraction sensing buttons so that those contraction sensing buttons that are located above active regions of patient's abdomen and uterus are analyzed, and those contraction sensing buttons near inactive regions of the patients abdomen (which are not above the current location of the uterus) may be de-emphasized or ignored.

Although contraction sensing button sensors that protrude somewhat perpendicular into the patient's skin in order to better feel the contractions of the muscular uterus below the skin are generally good for detecting uterine motion, contrast sensors that are disposed generally parallel to the patients skin may often be better disposed to sense the patient's ambient background movement. Such ambient background motion may be caused by non-uterine contraction motion, such as standing up, sitting down, bending and so on.

In some embodiments, the sensing belt may process signals from a plurality of uterine contraction sensors (generally disposed to protrude in a perpendicular manner somewhat into the patient's skin) along with signals from a plurality of ambient motion sensors generally disposed parallel to the patient's skin. The ambient motion sensors may, for example, be disposed in between individual contracting sensing buttons. In this way, for example, when the patient is bending, the skin parallel ambient motion sensors will generate a large signal. This signal that can be used to instruct the device's processor to deemphasize or ignore the signals from the contraction sensing buttons during this time. Other types of ambient motion signals, such as accelerometers, may also be used for this purpose.

Thus, as previously discussed, in one embodiment the device may be a uterine activity or contraction monitor device capable of being comfortably worn throughout the day. This monitor device may comprise a belt, such as an elastic belt, configured to fit around a pregnant patient's abdomen. This belt will have at least one, and often a plurality of, uterine contraction sensors. These uterine contraction sensors may often be protruding contraction sensing buttons, disposed generally perpendicular to the patient's skin, and designed to protrude somewhat into the patient's skin. These may be configured to monitor uterine contractions and produce uterine contraction signals.

As previously discussed, in order to avoid signal distortions caused by patient movement, which will be inevitable for devices intended to be worn throughout the day, this sensing belt will often have at least one ambient motion sensor configured to monitor non-uterine contraction movements and produce other movement (background movement) signals. These ambient motion sensors will often be disposed generally parallel to the patient's skin, and may for example be disposed between individual contracting sensing buttons. The device may often have other ambient motion sensors, such as accelerometers, to sense motion by other means and again de-emphasize signals from the uterine motion detecting sensors during periods of other motion.

As previously discussed, the device will often have a processor, such as a microprocessor and associated software, configured to correct the uterine contraction signals for distortions caused by the patient's movement, which are picked up by the other movement (background movement) sensors. The device will also often have either an onboard memory to store these various signals, a wireless transmitter or transceiver configured to transmit these signals to outside devices, or both. This wireless transmitter or transceiver can often be configured to conform to various low-power, limited range, digital transmission protocols, often in the 2.4 GHz range, such as the IEEE 802.15 standards including Bluetooth™, Zigbee™, and other protocols.

In an alternative embodiment, the invention may be a method for monitoring for complications of pregnancy. Indeed this method may be part of a comprehensive monitoring system. In one embodiment, the invention may comprise fitting a belt, such as an elastic belt, around the abdomen of a pregnant human for at least 12 hours a day. This belt may comprise or contain at least one uterine contraction sensor configured to monitor uterine contractions and produce uterine contraction signals. These may be the previously described contraction sensing buttons generally disposed perpendicular to the patient's abdominal skin, and may be protruding slightly into the abdomen.

Here, the belt may also contain at least one ambient motion sensor configured to monitor non-uterine contraction movements, and produce other movement signals. The method will generally use at least a first computer processor, such as a microprocessor, to correct the uterine contraction signals for distortions caused by other movement signals, such as ambient motion signals, thus producing corrected uterine contraction signals.

The method will also often involve using a wireless transmitter or receiver to transmit these corrected uterine contraction signals to another wireless capable pregnancy monitoring device, and receiving these corrected uterine contraction signals at this wireless pregnancy monitoring device. Alternatively the data may be stored in local memory, for example by using a removable memory card, stick or other device, and then transferred in this manner. There the method may use at least a second processor (microprocessor) to analyze these transmitted and corrected uterine contraction signals for a complication of pregnancy. This analysis may, for example, work to distinguish between contraction patterns due to normal Braxton Hicks contractions, and the contraction patterns due to more serious problems such as preterm labor. Thus either the belt or the wireless pregnancy warning device, or both devices, may then produce a warning message when a complication of pregnancy, such as preterm labor, is found.

Because the system will occasionally produce false alarms, it will also often be useful to have the system inform the patient both when normal contractions, such as Braxton-Hicks contractions are detected, and when abnormal uterine contractions, such as preterm labor, are suspected. The patient may review this data, and annotate this data with additional information such as what the patient was doing on or somewhat before the condition was reported. This will enable the patient to flag possible false alarms for herself and also for the her healthcare providers, as well as to indicate when alarms should be given higher priority—for example when abnormal contractions occurred when the patient was otherwise not doing anything unusual or remarkable.

FIG. 1 shows a uterine contraction monitoring belt (100) containing a plurality of soft, semi-soft, or semi-rigid projecting or protruding "fingers", "buttons" or "probes" (here called contraction sensing buttons) (102). The belt contains a buckle or other fastening mechanism (104) as well as typically a battery, a microprocessor, various signal processing electronics, and often a wireless transceiver or a data storage device (not shown). As previously discussed, the belt may be made of an elastic material, and buckle or other fastening mechanism may optionally contain pressure sensors, monitors or a pressure adjusting mechanism to ensure that the belt is pressing on the patient's abdomen with the optimal amount of pressure.

A close up of a contraction sensing button (102) is shown in (106). In this embodiment, the contraction sensing button may have one or more stretch sensors (108), such as resistance based elastic or fabric stretch sensors. These stretch sensors (108) may be disposed so that when worn around the abdomen of a patient, the sensors will be generally perpendicular to the skin of the patient, and also disposed to gently press into the skin of the patient, thus attempting to make good contact with the patient's muscles that in turn will expand or contract somewhat in response to contractions in the underlying uterus. Various types of sensors may be used to sense uterine contractions, including the capacitative sensors of Reinbold et. al., U.S. Pat. No. 6,033,370, MEMS pressure sensors, such as the sensors produced by Freescale Semiconductor, and fabric or elastic based stretch sensors such as the sensors of Fukui et. al., U.S. Pat. No. 4,715,235, and Jayaraman, U.S. Pat. No. 6,970,731, and others.

Also shown in the close up (106) are some ambient motion sensors (110) that, when the belt (100) is placed around a patient, will be disposed generally parallel to the patient's skin. Here the ambient motion sensors are shown disposed between the individual contraction sensing buttons (102).

Figure 2:
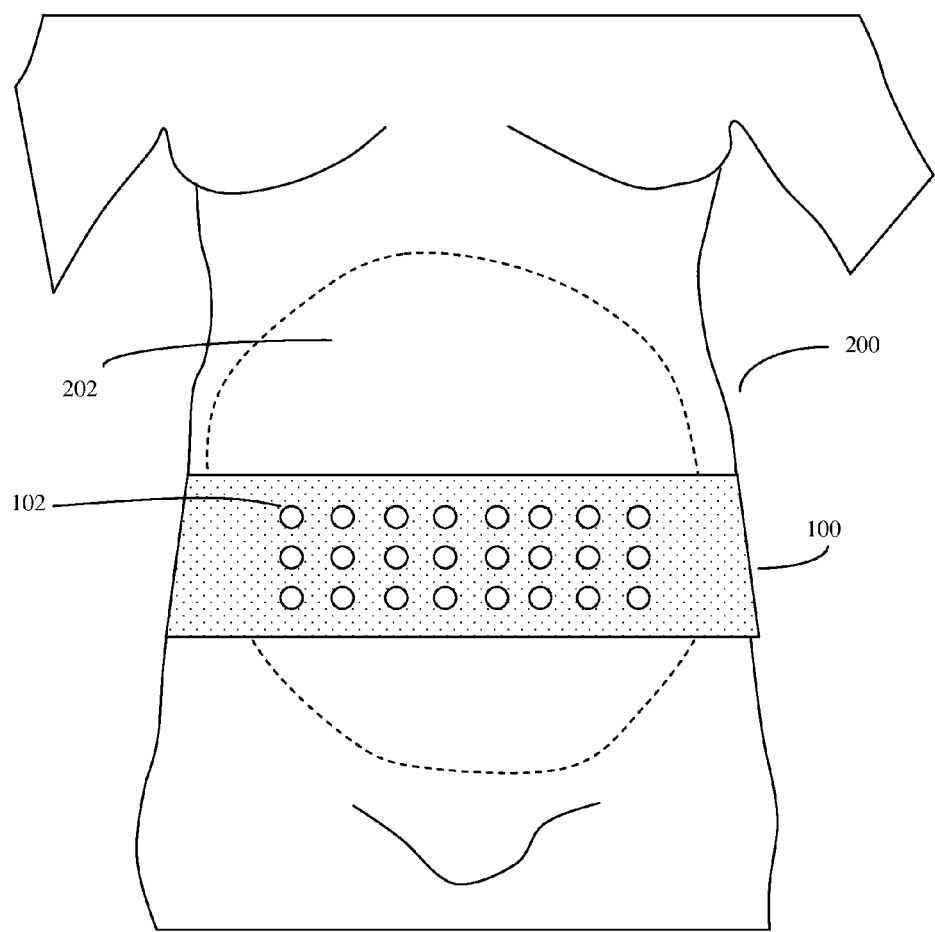
FIG. 2 shows how the flexible long-duration wear home uterine activity monitor may be worn by a pregnant patient.

FIG. 2 shows the uterine contraction monitoring belt (100) placed around the abdomen of a pregnant human patient (200). Here the various individual contraction sensing buttons (102) are placed above the pregnancy swollen part of the abdomen (202) above the uterus.

Figure 3:
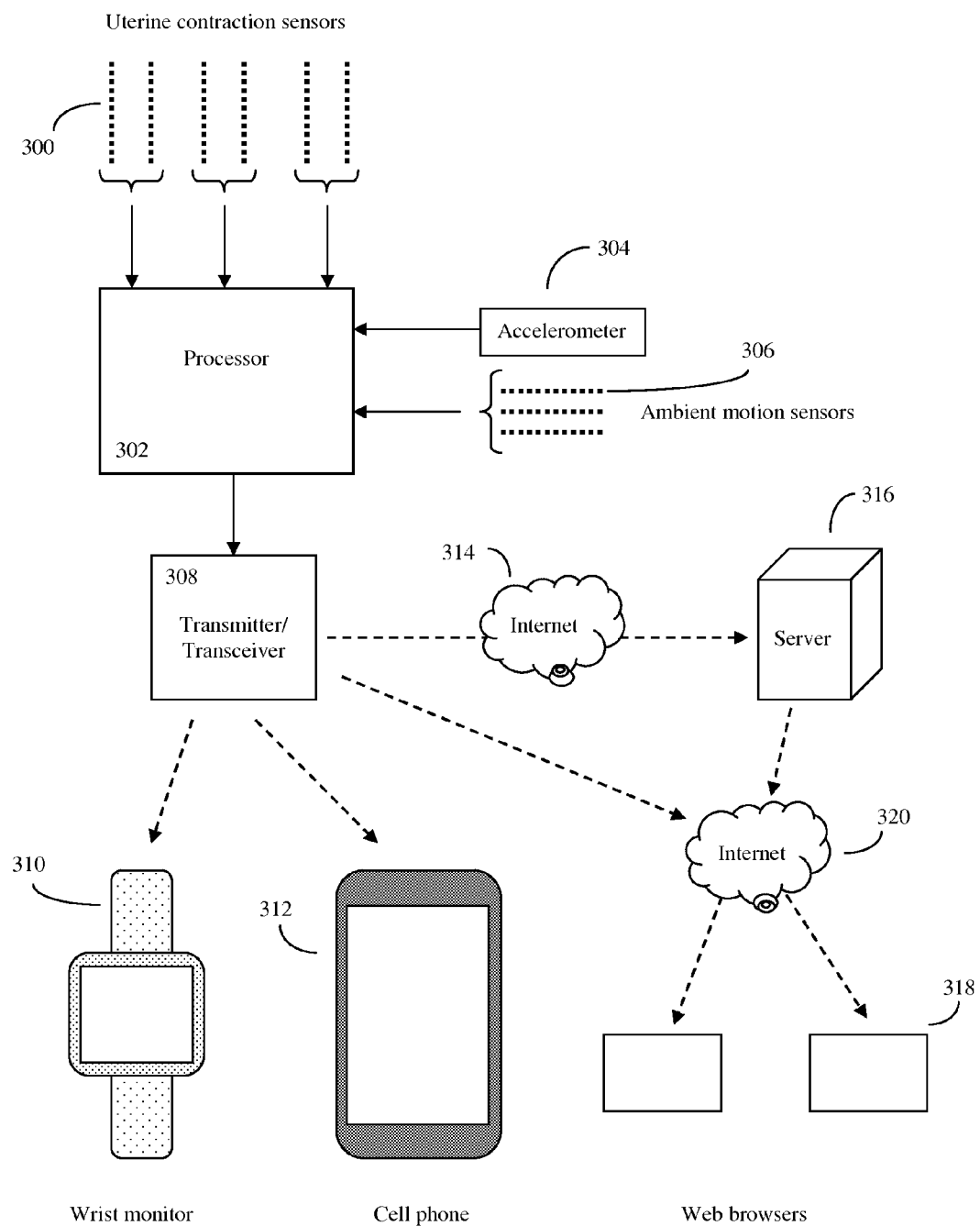
FIG. 3 shows one embodiment of the electronic and network components that may be used to implement a long-duration wear home uterine activity monitoring system.

FIG. 3 shows one embodiment of the various electrical and network components that may be used to implement a long-duration wear home uterine activity monitoring system. Here signals from various uterine contraction sensors (300), which may be resistance or MEMS or capacatitive sensors from the contraction sensing buttons earlier shown as (102) may be sent to processor (302), which often will be at least one microprocessor and associated software (not shown). In addition to signals from the uterine contraction sensors, ambient motion signals, which may originate from sensors such as an accelerometer (304) (e.g. a MEMS accelerometer) and/or from other ambient motion sensors generally disposed parallel to the patient's skin (306), such as the previously discussed sensors (110).

The processor (302) may determine which uterine contraction sensors (300) are most likely to give a good signal—i.e. accurately report on uterine contractions, and process this signal whenever the ambient motion sensors (304), (306) indicate that the uterine contraction signal has not been distorted by other patient motions. These corrected uterine contraction signals can then be wirelessly transmitted by transmitter or transceiver (308). As previously discussed, often this wireless transmission will be by low power digital transmissions, using protocols such as the Bluetooth™ protocol. However in some embodiments, the digital transmission may be by existing cellular telephone networks using various common cellular transmission protocols.

The uterine contraction sensors (300), processor (302), accelerometer (304), ambient motion sensors (306), and transmitter or transceiver (308) will often be part of the belt (100). By contrast, the other components such as the watch monitor (310), smart cell phone (312), Internet gateway, server (316) and computerized devices that may be running web browsers (318) will usually be separate from the belt.

The corrected uterine contraction signal data can be received by a variety of different devices, including a wristwatch like device (310), a smart cellular phone (e.g. an iPhone like device) (312), or the data can be transmitted through a wireless network gateway such as a wireless Internet router (not shown) over a first set of Internet connections (314) to remote servers, such as Internet web servers (316). These internet web servers (316) in turn can run various types of patient management software, can track trends, can allow healthcare professionals and others to view trends, issue tracking reports, and also issue warnings when the data indicates that abnormal uterine contractions have been observed. Various computerized devices, such as computers running web browsers (318) can receive the tracking reports and warnings issued by server (316) through alternate Internet connections (320). Alternately, the various computerized devices (318) can exchange information directly with transmitter or transceiver (308) without the user of server (316).

Figure 4:
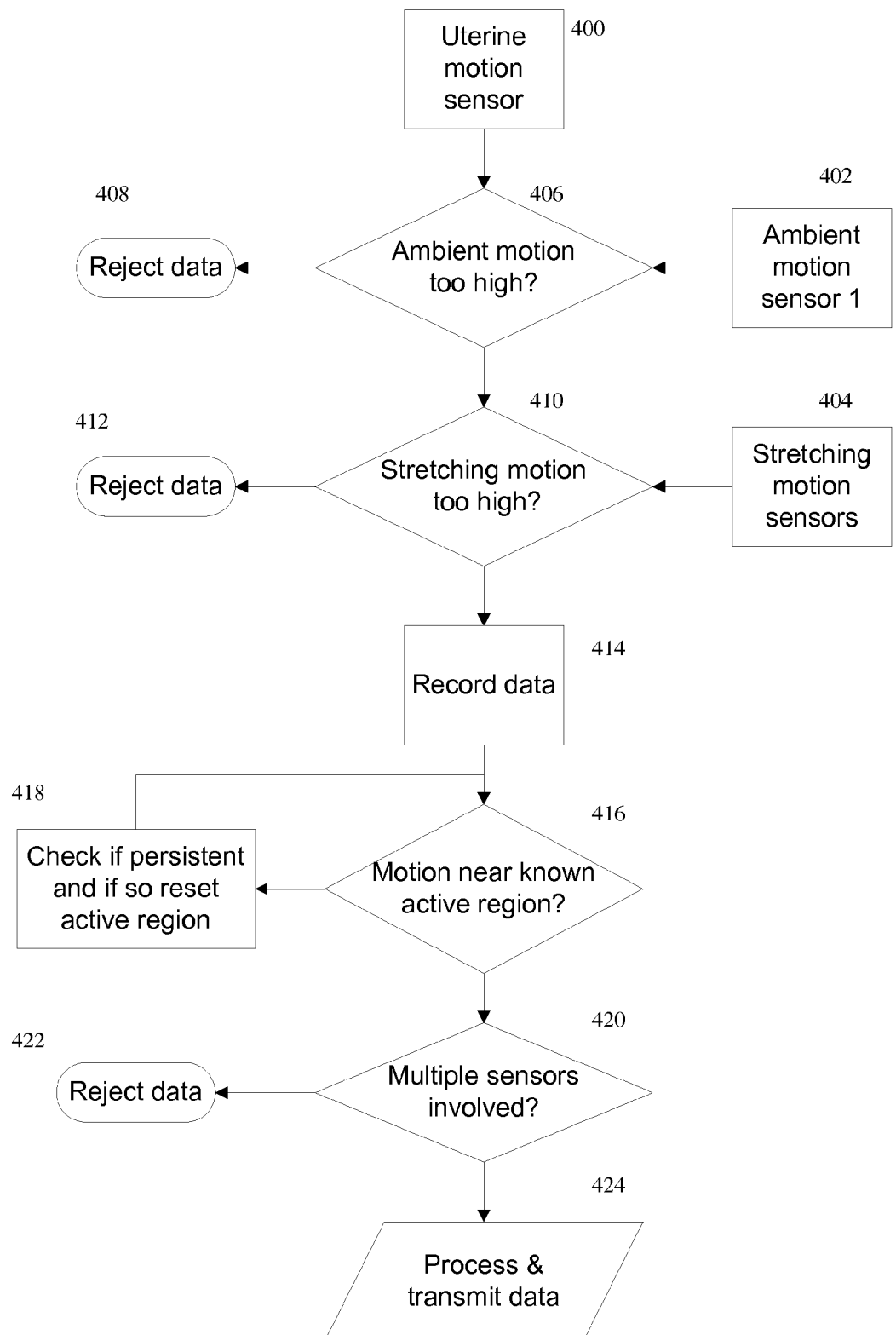
FIG. 4 shows one embodiment of the software and algorithms to subtract ambient background motion signals from uterine motion signals

FIG. 4 shows one embodiment of the software and algorithms that may be used to subtract ambient background motion signals from uterine motion signals. Here data from the uterine motion sensor(s) (400), which may be the individual contraction sensing buttons (102) and/or the uterine contraction sensors (300) are analyzed in the context of data obtained from one or more ambient motion sensors (402) and/or stretching motion sensors (404). In one embodiment, the ambient motion sensors (402) may be one or more accelerometers (304) such as MEMS accelerometers. In this embodiment, the system software at (406) may instruct processor (302) to, for example, ignore or deemphasize (408) the uterine contraction data if the ambient motion is too high. In a similar manner, if the stretching ambient motion sensor data (404), which may be obtained from the ambient motion sensors (110) and (306), is too high, the system software at (410) may again instruct processor (302) to ignore or deemphasize (412) the uterine contraction data. The uterine contraction data that can be trusted can then be recorded at least temporarily in the device's computer memory and then analyzed further.

As previously discussed, not all of the various contraction sensing buttons (102)/uterine contraction sensors (300) will be positioned properly above relevant portions of the uterus. The position of the belt and the various contraction sensing buttons (102)/uterine contraction sensors (300) will likely change somewhat on a day-to-day basis, because the user will most likely want to at least briefly remove the belt to shower or bathe, and when the belt is put on again, it will likely shift position. To compensate for these shifts, as well as changes in uterine position during pregnancy, the software may contain adaptive routines or algorithms to compensate for these shifts.

Thus in order to further improve the reliability of the analysis, data from sensors previously determined to be positioned near known active regions of the uterus (i.e. positioned properly) will generally be given higher preference. To do this, the system software may be configured to monitor which particular contraction sensors (102)/(300) that have recently been reliably generating typical uterine contraction signals, and emphasize this data for subsequent analysis. Indeed in some cases, data from sensors believed not to be above relevant portions of the uterus may be totally excluded. Here, for example, the software may check which uterine contraction data for particular uterine contraction sensors (102)/(300) has been persistent and which has not been persistent, and periodically determine which sensors should be used for the analysis (active), and periodically reset the active region (what contraction sensors are considered to be active) (418).

In order to further improve the reliability of the analysis, in some embodiments, the processor (302) and associated system software will correlate data (420) obtained from multiple contraction sensors (102)/(300) known to be properly positioned above active regions of the uterus, and use various signal processing techniques (e.g. signal averaging, correlation, difference analysis, and the like) and reject or deemphasize data (422) from those contraction sensors (102)/(300) that does not correlate well with the other contraction sensors (102)/(300).

The data from the various contraction sensors may be stored in computer memory onboard the belt and then may also be wirelessly transmitted (424) to various devices including the previously discussed wristwatch like device (310), a smart cellular phone (e.g. an iPhone like device) (312), or wireless network gateway(s), remote web servers (316), computers running web browsers (318), and the like. Alternatively or additionally, the data may be stored in removable memory media, such as removable (plug in) memory chips, cards, and the like, and periodically transferred to other devices in this manner.

Once the processed uterine contraction data has been transmitted (424), the data will then often be further analyzed by various outside devices and often by healthcare professionals, such as the patient's physician.

Figure 5:
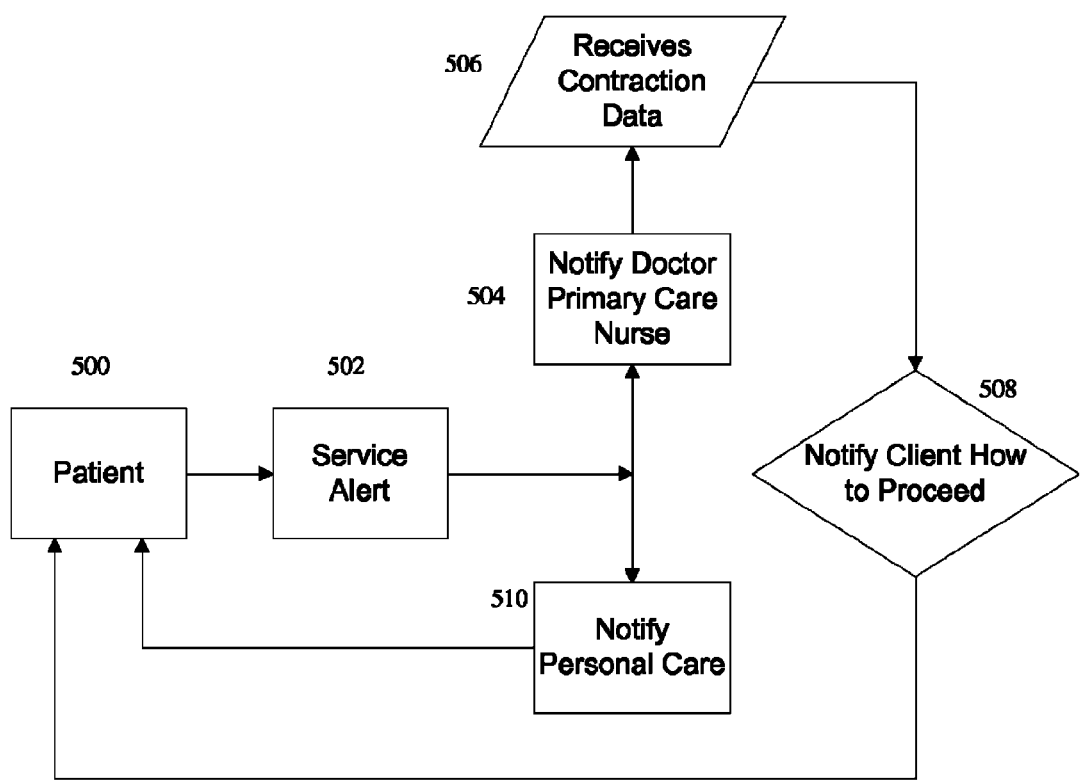
FIG. 5 shows an example of a system for alerting the patient (client) on how to proceed in response to various types of uterine contraction data.

FIG. 5 shows an example of a system for alerting the patient (client) as to how to proceed in response to various types of uterine contraction data. This system may, for example, run on web server (316), and be used by various users (e.g. healthcare professionals, or the patient herself) running web browsers (318). In this example, data transmitted by a patient, previously shown as (424), may be analyzed for the presence of uterine contraction abnormalities, such as the onset of premature labor, by any of a variety of different devices. This analysis may be done by the processor or processors (302) that are in turn part of belt (100), or alternatively by other devices, for example by wristwatch like device (310), a smart cellular phone (e.g. an iPhone like device) (312), or remote web servers (316).

In the FIG. 5 example, data from patient (500), such as data transmitted in step (424) may be transmitted to any one of devices (310), (312), (316), where it may be further analyzed for these previously discussed uterine contraction abnormalities. If an abnormal pattern is found, the device may generate a service alert (502) indicating that there may be a problem. This service alert (502) may, for example, be generated by a monitoring service that is making use of a remote web server such as (316). The monitoring service may in turn then either manually or automatically notify the patient's doctor, primary care nurse, or other healthcare professional (504) to notify them of the problem, and the healthcare professional may then receive a partial or full copy of the patient's contraction data as well (506). Upon review, the healthcare professional may then notify the client how best to proceed (508) in view of the data. Here any data that has been annotated by the patient may also be considered by the healthcare analysis. Thus, for example, if an abnormal contraction was noticed but the patient annotates the data with a notation that the patient had just put on the belt, the healthcare professional may know that this particular indication is likely to be a false alarm.

To expand on this discussion, note that in order to reliably detect abnormal uterine contraction problems that are indicative of medical emergencies, such as preterm labor, the system will often need to be set at a sensitivity level that occasionally will generate false positive results. Additionally, the patient may experience normal Braxton Hicks contractions as well. As yet another possibility, the patient may accidentally trigger the system during periods of normal activity, such as putting on and taking off the belt. In these situations, the service alert (502) may additionally or alternatively be set to notify the patient first by an alternative personal care method (510), such as by an alert on the patient's wristwatch like device (310), or smart cellular phone device (312). This alternative communications path can give the patient (500) feedback about what type of uterine contractions were observed, and the patient in turn can annotate this data. For example, if the patient has accidentally triggered the device while taking the belt on and off, the patient could, for example, inform the system that the observed event was a false alarm. Alternatively, if for example the patient was resting, and a service alert (502) was generated, the patient after notification by the personal care communications path (510) might annotate the data with the comments that the patient was not doing anything that might be expected to trigger a false alarm. In this manner, the quality of the data going to the healthcare professional (504) can be improved, resulting in fewer false alarms and more prompt and effective action in the event that a medically significant event, such as preterm labor, has occurred.

The invention claimed is:

1. A method for monitoring for complications of pregnancy, comprising:
fitting a belt around the abdomen of a pregnant human for at least 12 hours a day, said belt containing at least one uterine contraction sensor configured to monitor uterine contractions and produce uterine contraction signals;
said belt containing at least one ambient motion sensor configured to monitor non-uterine contraction movements and produce other movement signals;
using a first processor to correct said uterine contraction signals for distortion caused by said other movement signals, thus producing corrected uterine contraction signals;
wirelessly transmitting said corrected uterine contraction signals to a wireless pregnancy monitoring device;
wirelessly receiving said corrected uterine contraction signals;
using a second processor to analyze said corrected uterine contraction signals for a complication of pregnancy;
and producing a warning message when a complication of pregnancy is detected.

2. The method of claim 1, wherein said complication of pregnancy is premature labor.

3. The method of claim 1, wherein said first or second processor distinguishes between a complication of pregnancy and normal Braxton Hicks contractions.

4. The method of claim 1, wherein said wireless pregnancy monitoring device is a cellular phone running pregnancy monitoring software.

5. The method of claim 1, wherein said wireless pregnancy monitoring device is configured to resemble a wristwatch.

6. The method of claim 1, wherein said wireless pregnancy monitoring device transmits said corrected uterine contraction signals over the internet to a remote patient management website.

7. The method of claim 1, in which the belt is an elastic belt.

8. The method of claim 1, in which the belt contains belt pressure sensor or adjustment device that enables the patient to consistently adjust the belt to achieve a uniform degree of pressure.

9. The method of claim 1, in which said first or second processor are configured to enable said pregnant human to annotate said corrected uterine contraction signals with additional data indicative of the pregnant human's status.

* * * * *